US012599639B2

(12) United States Patent (10) Patent No.: US 12,599,639 B2
Nakano et al. (45) Date of Patent: Apr. 14, 2026

(54) JOINT FUNCTION-IMPROVING COMPOSITION

(71) Applicant: MEGMILK SNOW BRAND CO., LTD., Hokkaido (JP)

(72) Inventors: Ayatake Nakano, Hokkaido (JP); Takehiko Yasueda, Hokkaido (JP); Yasuyuki Seto, Hokkaido (JP)

(73) Assignee: MEGMILK SNOW BRAND CO., LTD., Hokkaido (JP)

( * ) Notice: Subject to any disclaimer, the term of this patent is extended or adjusted under 35 U.S.C. 154(b) by 342 days.

(21) Appl. No.: 18/271,259

(22) PCT Filed: Jan. 7, 2022

(86) PCT No.: PCT/JP2022/000313
§ 371 (c)(1),
(2) Date: Jul. 7, 2023

(87) PCT Pub. No.: WO2022/163323
PCT Pub. Date: Aug. 4, 2022

(65) Prior Publication Data
US 2024/0075081 A1 Mar. 7, 2024

(30) Foreign Application Priority Data

Jan. 26, 2021 (JP) ................................. 2021-010460

(51) Int. Cl.
| A61K 35/747 | (2015.01) |
| A61K 35/745 | (2015.01) |
| A61P 19/02 | (2006.01) |
| C12N 1/205 | (2026.01) |
| C12R 1/23 | (2006.01) |
| C12R 1/46 | (2006.01) |

(52) U.S. Cl.
CPC .......... *A61K 35/747* (2013.01); *A61K 35/745* (2013.01); *A61P 19/02* (2018.01); *C12N 1/205* (2021.05); *C12R 2001/23* (2021.05); *C12R 2001/46* (2021.05)

(58) Field of Classification Search
CPC ..... A61K 35/747; A61K 35/745; A61P 19/02; C12N 1/205; C12R 2001/46; C12R 2001/23
See application file for complete search history.

(56) References Cited

U.S. PATENT DOCUMENTS

| 9,504,720 B2 | 11/2016 | Itoh et al. |
| 2002/0141977 A1 | 10/2002 | Collins et al. |
| 2006/0088514 A1 | 4/2006 | O'Mahony et al. |
| 2008/0038228 A1 | 2/2008 | Rautonen et al. |
| 2011/0027348 A1 | 2/2011 | Feher |
| 2013/0316032 A1 | 11/2013 | Itoh et al. |
| 2019/0231829 A1 | 8/2019 | Goodman et al. |

| 2020/0093872 A1 | 3/2020 | Zuscik et al. |
| 2020/0289587 A1 | 9/2020 | Kiely et al. |
| 2021/0023145 A1 | 1/2021 | Wood et al. |
| 2021/0154244 A1 | 5/2021 | Ji et al. |

FOREIGN PATENT DOCUMENTS

| CN | 104546944 A | 4/2015 |
| CN | 112023030 A | 12/2020 |
| CN | 112155207 A | 1/2021 |
| EP | 3757207 A1 | 12/2020 |
| JP | H06-217713 A | 8/1994 |
| JP | 10-84909 A | 4/1998 |
| JP | 2004-91433 A | 3/2004 |
| JP | 2007-507485 A | 3/2007 |
| JP | 2012-158568 A | 8/2012 |
| JP | 2015-86214 A | 5/2015 |
| JP | 2015-96555 A | 5/2015 |
| JP | 2020-94015 A | 6/2020 |
| KR | 10-2013-0045511 A | 5/2013 |

(Continued)

OTHER PUBLICATIONS

Liu et al. (Journal of Interferon and Cytokine Research, vol. 36 No. 12, pp. 706-712).*
Extended European Search Report dated Mar. 18, 2025, issued in European patent application No. 22745550.8.
Supplemental Partial European Search Report dated Nov. 25, 2024, issued in European patent application No. 22745550.8.
Office Action dated Jul. 8, 2025 issued in Chinese patent application No. 202280011725.3, with English machine translation thereof.
Office Action dated May 22, 2025 in Taiwanese patent application No. 111101373, with English machine translation thereof.
Office Action dated Feb. 12, 2025, issued in Taiwanese patent application No. 111101373, with English machine translation thereof.
Office Action dated Aug. 6, 2025 issued in Indonesian patent application No. P00202306152, with English translation thereof.
Yamashita, M. et al., "Preventive Effect of *Lactobacillus helveticus* SBT2171 on Collagen-Induced Arthritis in Mice," *Frontiers in Microbiology*, 2017, vol. 8, article 1159, pp. 1-12.

(Continued)

*Primary Examiner* — Robert A Zeman
(74) *Attorney, Agent, or Firm* — GREENBLUM & BERNSTEIN, P.L.C.

(57) ABSTRACT

An object is to provide a joint function-improving composition which is useful for prevention or treatment of various arthropathies such as osteoarthritis including knee osteoarthritis as a typical example and rheumatoid arthritis because the composition has an action of promoting growth of chondrocytes and an action of suppressing the production of an inflammation factor, a cartilage matrix degradation factor, a pain factor or a neuronal outgrowth factor by synoviocytes and to provide a joint function-improving product containing the composition such as a food or a drink, feed and a medicine. A joint function-improving composition containing bacterial cells and/or a culture of a bacterium belonging to genera *Lactobacillus, Lactococcus, Streptococcus* or *Bifidobacterium* and a joint function-improving agent, a joint function-improving food or drink, a joint function-improving nutritional composition, joint function-improving feed or a joint function-improving pharmaceutical agent which is characterized by containing the joint function-improving composition.

1 Claim, No Drawings

Specification includes a Sequence Listing.

(56) References Cited

FOREIGN PATENT DOCUMENTS

| | | |
|---|---|---|
| KR | 10-2018-0103772 A | 9/2018 |
| KR | 10-2018-0104544 A | 9/2018 |
| KR | 10-2020-0131658 A | 11/2020 |
| WO | 2009/095240 A1 | 8/2009 |
| WO | 2018/180728 A1 | 10/2018 |
| WO | 2019/099682 A1 | 5/2019 |
| WO | 2019/145570 A1 | 8/2019 |
| WO | 2019/178309 A1 | 9/2019 |
| WO | 2021/112041 A1 | 6/2021 |

OTHER PUBLICATIONS

Amdekar, S. et al., "Transcriptional activity of cytokines induced by oral administration of *Lactobacillus casei* and *Lactobacillus acidophilusin* experimental model of arthritis," *AIMS Molecular Science*, 2017, vol. 4, No. 2, pp. 164-174.

Lee, S.H. et al., ":*Lactobacillus acidophilus* ameliorates pain and cartilage degradation in experimental osteoarthritis," *Immunology Letters*, 2018, vol. 203, pp. 6-14.

Jhun, J. et al., "Combinatmarion treatment with *Lactobacillus acidophilus* LA-1, vitamin B, and curcumin ameliorates the progression of osteoarthritis by inhibiting the pro-inflammatory mediators," *Immunology Letters*, 2020, vol. 228, pp. 112-121.

Zamani, B. et al., "Synbiotic supplementation and the effects on clinical and metabolic responses in patients with rheumatoid arthritis: a randomised, double-blind, placebo-controlled trial," *British Journal of Nutrition*, 2017, vol. 117, pp. 1095-1102.

Sheil, B. et al., "Is the mucosal route of administration essential for probiotic function? Subcutaneous administration is associated with attenuation of murine colitis and arthritis," *Gut*, 2004, vol. 53, pp. 694-700.

Achi, S.C. et al., "Prophylactic effects of probiotic *Bifidobacterium* spp. in the resolution of inflammation in arthritic rats,", *Applied Microbiology and Biotechnology*, 2019, vol. 103, pp. 6287-6296.

Henrotin, Y et al., "Protective Actions of Oral Administration of *Bifidobacterium longum* CBi0703 in Spontaneous Osteoarthritis in Dunkin Hartley Guinea Pig Model," *Cartilage*, 2019, vol. 13 (Suppl. 2), pp. 1204S-1213S.

Kakadiya, P. et al., "Anti-Rheumatoid Activity of Cell Wall Contents of *Lactococcus lactis* Subsp. *cremoris*," *International Journal of Pharma and Bio Sciences*, 2014, vol. 5, No. 4, pp. B-118 to B-127.

International Search Report issued in PCT/JP2022/000313, dated Mar. 22, 2022, and English translation thereof.

International Preliminary Report on Patentability issued in PCT/JP2022/000313, dated Jul. 31, 2023, including Written Opinion dated Mar. 9, 2022, and English translation thereof.

Office Action dated Dec. 16, 2025, issued in Japanese patent application No. 2022-578206, with English machine translation thereof.

Office action dated Jan. 28, 2026, issued in Chinese patent application No. 202280011725.3, with English machine translation.

* cited by examiner

```
                        SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
gaggccaagc cctggtatg                                          19

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
cgggccgatt gatctcagc                                          19

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
ctgggctaca ctgagcacc                                          19

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
aagtggtcgt tgagggcaat g                                       21

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
tcctgatgtg ggtgaataca atg                                     23

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
gccatcgtga agtctggtaa aat                                     23
```

-continued

```
<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
atgctgacta tggctacaaa agc                                                  23

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
tcgggcaatc atcaggcac                                                       19

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ggcagacccg caacattact                                                      20

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
caccaccgac ctcgaagtc                                                       19
```

JOINT FUNCTION-IMPROVING COMPOSITION

TECHNICAL FIELD

The present invention relates to a joint function-improving composition which can improve joint function. The invention has an action of promoting growth of chondrocytes and an action of suppressing the production of an inflammation factor, a cartilage matrix degradation factor, a pain factor or a neuronal outgrowth factor by synoviocytes. According to the invention, a material having a joint function-improving action which is useful for prevention or treatment of various arthropathies such as osteoarthritis including knee osteoarthritis as a typical example and rheumatoid arthritis can be provided. The invention further relates to a joint function-improving agent, a joint function-improving food or drink, a joint function-improving nutritional composition, joint function-improving feed or a joint function-improving pharmaceutical agent containing the material having a joint function-improving action.

BACKGROUND ART

The average lifespan of Japanese people has recently exceeded 80 years, and the country has entered a super-aged society where about one in four is the age of 65 or older. Accordingly, the incidence rate of motor disorders is steadily increasing. In 2007, the Japanese Orthopaedic Association has proposed a new term "locomotive syndrome" to change the attitude of the citizens and the doctors towards maintenance and improvement of the health of locomotorium and care. The locomotive syndrome refers to a state in need of long-term care and a state at an increased risk of requiring long-term care due to locomotive dysfunction, and locomotor organs generally include organs having the role of supporting and moving the body, such as bones, joints, ligaments, spines, the spinal cord, muscles, tendons and peripheral nerves. Typical diseases and functional impairment found in the locomotor organs include osteoporosis, sarcopenia, osteoarthritis and the like.

The number of patients with knee osteoarthritis in this country was estimated at around 25.3 million in 2009. It is said that 20 to 30% of the population aged 50 or older suffer therefrom, and knee osteoarthritis is an arthropathy with the highest patient number. Factors causing osteoarthritis are believed to be degeneration of joint components due to aging and genetic factors, loads to joints due to obesity, labor and sport and the like. Deformation of a joint, including a decrease or loss of cartilage, is accelerated as inflammation is caused in the synovial tissue surrounding the joint with the onset of osteoarthritis. With the concurrent inflammation and the deformation of the joint, many osteoarthritis patients suffer from pain, and their QOL (quality of life) decreases considerably.

Because articular cartilage does not have any vessels or neurons, its spontaneous recovery is considered to be difficult once articular cartilage is damaged. Thus, when the symptoms of osteoarthritis are mild, a physical therapy such as thermotherapy and traction or a palliative care using an analgesic drug or an anti-inflammatory drug is used. The existing steroid and nonsteroid anti-inflammatory drugs, however, have a serious problem of side effects such as adrenal insufficiency and small intestinal disorder. When the symptoms are severe, infusion of hyaluronic acid into the joint or a joint replacement is applied. In order to relieve the symptoms of osteoarthritis and to improve the QOL of the patient in the daily life, however, in view of the nature of the disease, it is required for the patient by him or herself to maintain the shape of the cartilage, prevent or repair the deformation the cartilage, or regenerate the lost cartilage and to suppress inflammation and pain around the joint through daily, safe and long-term intake of a food or an active ingredient contained in a food.

A joint function-improving agent characterized by containing a *Lycium* extract has been disclosed so far (Patent Document 1). However, it has not been known so far that a bacterial cell component or a culture of a lactic acid bacterium or a *Bifidobacterium* species directly acts on chondrocytes or synoviocytes and thus promotes the growth of chondrocytes and suppresses the production of an inflammation factor, a cartilage matrix degradation factor, a pain factor or a neuronal outgrowth factor by synoviocytes.

CITATION LIST

Patent Literature

Patent Document 1: JP2020-94015A

SUMMARY OF INVENTION

Technical Problem

An object of the invention is to provide a material which can be taken daily and safely for a long term and which has an action of promoting growth of chondrocytes, an excellent effect of repairing or regenerating deformed or lost cartilage and relieving pain and a joint function-improving action. Another object of the invention is to provide a material having an action of suppressing the production of an inflammation factor, a cartilage matrix degradation factor, a pain factor or a neuronal outgrowth factor by synoviocytes. The material is useful for prevention or treatment of various arthropathies such as osteoarthritis including knee osteoarthritis as a typical example and rheumatoid arthritis. Another object of the invention is to provide a joint function-improving agent, a joint function-improving food or drink, a joint function-improving nutritional composition, joint function-improving feed or a joint function-improving pharmaceutical agent in which a material having a joint function-improving action is blended. The material has an action of promoting growth of chondrocytes. Moreover, the material has an action of suppressing the production of an inflammation factor, a cartilage matrix degradation factor, a pain factor or a neuronal outgrowth factor by synoviocytes and thus has an excellent effect of repairing or regenerating deformed or lost cartilage and relieving pain.

Solution to Problem

As a result of progressing extensive study to achieve the objects, the present inventors have found that some lactic acid bacteria or bifidobacteria have an action of promoting growth of chondrocytes or an action of suppressing the production of an inflammation factor, a cartilage matrix degradation factor, a pain factor or a neuronal outgrowth factor by synoviocytes, and the invention has been thus completed.

That is, the invention has the following features.

(1) A joint function-improving composition containing bacterial cells and/or a culture of a bacterium belonging to genera *Lactobacillus, Lactococcus, Streptococcus* or *Bifidobacterium* as an active ingredient.

(2) The joint function-improving composition of (1) which is characterized in that the bacterium belonging to genera *Lactobacillus, Lactococcus, Streptococcus* or *Bifidobacterium* is one or more selected from *Lactobacillus acidophilus, Lactobacillus helveticus, Lactobacillus salivarius, Lactococcus lactis, Lactococcus laudensis, Streptococcus oralis, Bifidobacterium longum, Bifidobacterium pseudolongum* and *Bifidobacterium thermophilum.*

(3) The joint function-improving composition of (2) which is characterized in that the bacterium belonging to *Lactobacillus salivarius, Lactococcus lactis* or *Bifidobacterium longum* is a bacterium belonging to *Lactobacillus salivarius* subsp. *salivarius, Lactococcus lactis* subsp. *lactis, Lactococcus lactis* subsp. *cremoris* or *Bifidobacterium longum* subsp. *infantis.*

(4) The joint function-improving composition described in any one of (1) to (3) which is characterized in that the bacterium belonging to genera *Lactobacillus, Lactococcus, Streptococcus* or *Bifidobacterium* is one or more selected from *Lactobacillus acidophilus* strain SBT2062 (FERM BP-11075), *Lactobacillus helveticus* strain SBT2161 (NITE BP-1707) and strain SBT2171 (FERM BP-5445), *Lactobacillus salivarius* strain SBT2687 (NITE ABP-03331) and strain SBT2651 (NITE P-03330), *Lactobacillus salivarius* subsp. *salivarius* strain SBT2670 (FERM P-13247), *Lactococcus lactis* subsp. *lactis* strain SBT0625 (NITE P-03078), *Lactococcus lactis* subsp. *cremoris* strain SBT11373 (NITE P-03246), *Lactococcus laudensis* strain SBT11178 (NITE P-03333), *Streptococcus oralis* strain SBT0320 (NITE P-03332), *Bifidobacterium longum* strain SBT2928 (FERM P-10657), *Bifidobacterium longum* subsp. *infantis* strain SBT2785 (NITE P-03328), *Bifidobacterium pseudolongum* strain SBT2922 (NITE P-02984) and *Bifidobacterium thermophilum* strain SBT2992 (NITE P-03364).

(5) A joint function-improving agent, a joint function-improving food or drink, a joint function-improving nutritional composition, joint function-improving feed or a joint function-improving pharmaceutical agent which is characterized by containing the joint function-improving composition described in any one of (1) to (4).

(6) A novel lactic acid bacterium, *Lactobacillus salivarius* strain SBT2687.

(7) A novel lactic acid bacterium, *Lactobacillus salivarius* strain SBT2651.

(8) A novel lactic acid bacterium, *Lactococcus laudensis* strain SBT11178.

(9) A novel lactic acid bacterium, *Streptococcus oralis* strain SBT0320.

(10) A novel *Bifidobacterium* strain, *Bifidobacterium longum* subsp. *infantis* strain SBT2785.

(11) A novel *Bifidobacterium* strain, *Bifidobacterium thermophilum* strain SBT2992.

(12) Use of bacterial cells and/or a culture of a bacterium belonging to genera *Lactobacillus, Lactococcus, Streptococcus* or *Bifidobacterium* for the manufacture of a joint function-improving composition.

(13) Bacterial cells and/or a culture of a bacterium belonging to genera *Lactobacillus, Lactococcus, Streptococcus* or *Bifidobacterium* for use in the improvement of joint function.

(14) A method for improving joint function comprising causing a subject in need thereof to take an effective amount of bacterial cells and/or a culture of a bacterium belonging to genera *Lactobacillus, Lactococcus, Streptococcus* or *Bifidobacterium* or administering an effective amount of the bacterial cells and/or the culture to the subject.

(15) A composition for promoting growth of chondrocytes, suppressing production of an inflammation factor, suppressing production of a cartilage matrix degradation factor, suppressing production of a pain factor and/or suppressing production of a neuronal outgrowth factor containing bacterial cells and/or a culture of a bacterium belonging to genera *Lactobacillus, Lactococcus, Streptococcus* or *Bifidobacterium* as an active ingredient.

Advantageous Effects of Invention

The joint function-improving composition of the invention is highly safe and has a significant joint function-improving action through an action of promoting growth of chondrocytes or an action of suppressing the production of an inflammation factor, a cartilage matrix degradation factor, a pain factor or a neuronal outgrowth factor by synoviocytes. The joint function-improving composition is useful for prevention or treatment of various arthropathies such as osteoarthritis including knee osteoarthritis as a typical example and rheumatoid arthritis. Moreover, the invention can improve the function of a joint. The invention has an action of promoting growth of chondrocytes and has an action of suppressing the production of an inflammation factor, a cartilage matrix degradation factor, a pain factor or a neuronal outgrowth factor by synoviocytes. Thus, the invention provides a joint function-improving agent, a joint function-improving food or drink, a joint function-improving nutritional composition, joint function-improving feed or a joint function-improving pharmaceutical agent in which a joint function-improving composition that is useful for prevention or treatment of various arthropathies such as osteoarthritis including knee osteoarthritis as a typical example and rheumatoid arthritis is blended.

DESCRIPTION OF EMBODIMENTS

As the lactic acid bacterium which can be used in the invention, any lactic acid bacterium which has a joint function-improving action and which belongs to genera *Lactobacillus, Lactococcus* or *Streptococcus* can be used, and as the bacteria of *Bifidobacterium*, any bacteria of *Bifidobacterium* which has a joint function-improving action and which belongs to genus *Bifidobacterium* can be used.

Examples of the lactic acid bacterium belonging to genus *Lactobacillus* include lactic acid bacteria belonging to *Lactobacillus acidophilus, Lactobacillus helveticus, Lactobacillus salivarius* and the like. Examples of the lactic acid bacterium belonging to genus *Lactococcus* include lactic acid bacteria belonging to *Lactococcus lactis, Lactococcus laudensis* and the like. Examples of the lactic acid bacterium belonging to genus *Streptococcus* include lactic acid bacteria belonging to *Streptococcus oralis* and the like. Examples of the bacteria belonging to genus *Bifidobacterium* include bacteria of *Bifidobacterium longum, Bifidobacterium pseudolongum, Bifidobacterium thermophilum* and the like. Examples of the lactic acid bacterium belonging to *Lactobacillus salivarius* include lactic acid bacteria such as *Lactobacillus salivarius* subsp. *salivarius.* Examples of the lactic acid bacterium belonging to *Lactococcus lactis* include lactic acid bacteria such as *Lactococcus lactis* subsp. *lactis* and *Lactococcus lactis* subsp. *cremoris.* Examples of the bacteria of *Bifidobacterium longum* include bacteria of *Bifidobacterium longum* subsp. *infantis*. The lactic acid bacterium or the bacteria of *Bifidobacterium* is not limited to those cited as examples.

*Lactobacillus acidophilus, Lactobacillus helveticus, Lactobacillus salivarius, Lactobacillus salivarius* subsp. *salivarius, Lactococcus lactis* subsp. *lactis, Lactococcus lactis* subsp. *cremoris, Lactococcus laudensis, Streptococcus oralis, Bifidobacterium longum, Bifidobacterium longum* subsp. *infantis, Bifidobacterium pseudolongum* and *Bifidobacterium thermophilum* which can be used in the invention can be classified by a general classification method such as analysis of the 16S ribosomal RNA gene sequence.

In the invention, *Lactobacillus acidophilus* strain SBT2062 (FERM BP-11075), *Lactobacillus helveticus* strain SBT2161 (NITE BP-1707) and strain SBT2171 (FERM BP-5445), *Lactobacillus salivarius* strain SBT2687 (NITE ABP-03331) and strain SBT2651 (NITE P-03330), *Lactobacillus salivarius* subsp. *salivarius* strain SBT2670 (FERM P-13247), *Lactococcus lactis* subsp. *lactis* strain SBT0625 (NITE P-03078), *Lactococcus lactis* subsp. *cremoris* strain SBT11373 (NITE P-03246), *Lactococcus laudensis* strain SBT11178 (NITE P-03333), *Streptococcus oralis* strain SBT0320 (NITE P-03332), *Bifidobacterium longum* strain SBT2928 (FERM P-10657), *Bifidobacterium longum* subsp. *infantis* strain SBT2785 (NITE P-03328), *Bifidobacterium pseudolongum* strain SBT2922 (NITE P-02984) and *Bifidobacterium thermophilum* strain SBT2992 (NITE P-03364) are particularly preferably used, but the invention is not limited thereto.

The joint function-improving composition of the invention can contain one or more of bacterial cells and cultures of bacteria belonging to genera *Lactobacillus, Lactococcus, Streptococcus* or *Bifidobacterium*. The active ingredient of the invention may be composed of bacterial cells of a bacterium belonging to genera *Lactobacillus, Lactococcus, Streptococcus* or *Bifidobacterium*. The active ingredient of the invention may be composed of a culture of a bacterium belonging to genera *Lactobacillus, Lactococcus, Streptococcus* or *Bifidobacterium*.

(Culture Method of Lactic Acid Bacterium or Bacteria of *Bifidobacterium*)

The lactic acid bacterium or the bacteria of *Bifidobacterium* used in the invention can be cultured according to a general method for culturing a lactic acid bacterium or bacteria of *Bifidobacterium*. For the culture medium, various media such as a milk medium, a medium containing a milk component and a semisynthetic medium which does not contain the same can be used. Examples of such media include a reduced skim milk medium and the like. Bacterial cells isolated from the obtained culture by cell collection means such as centrifugation can be directly used as an active ingredient of the invention. Bacterial cells after concentration, drying, lyophilization or the like can also be used, and dead cells obtained by heat drying or the like may also be used.

As the bacterial cells, not only those which are purely isolated but also a culture, a suspension, another bacterial cell-containing material and a cytoplasm or cell wall fraction obtained by treating bacterial cells using an enzyme or physical means can also be used. Examples of the form of the culture or the like include not only a culture using a medium that is generally used for culturing lactic acid bacteria, such as MRS medium (manufactured by DIFCO), M17 medium (manufactured by DIFCO) and 1% glucose-containing GAM medium (manufactured by Nissui Pharmaceutical Co., Ltd.), which are synthetic media, and a reduced skim milk medium, but also dairy products such as cheese, fermented milk and lactic acid bacteria beverages and the like, although the form is not particularly limited. Furthermore, a culture supernatant prepared by removing milk protein precipitates and bacterial cell components from the obtained culture using a method such as centrifugation and filtration operation and the like can also be used. Because the supernatant has a low solid content, the range of application to foods, drinks and the like becomes wide. For example, a culture supernatant can be prepared by centrifuging a reduced skim milk medium culture at 5,000 rpm for 10 minutes.

(Novel Lactic Acid Bacterium Strains or Novel *Bifidobacterium* Strains)

The invention relates to novel lactic acid bacterium strains or novel *Bifidobacterium* strains. The novel lactic acid bacterium strains or the novel *Bifidobacterium* strains are *Lactobacillus salivarius* strain SBT2687 (NITE ABP-03331), *Lactobacillus salivarius* strain SBT2651 (NITE P-03330), *Lactococcus laudensis* strain SBT11178 (NITE P-03333), *Streptococcus oralis* strain SBT0320 (NITE P-03332), *Bifidobacterium longum* subsp. *infantis* strain SBT2785 (NITE P-03328) and *Bifidobacterium thermophilum* strain SBT2992 (NITE P-03364). The lactic acid bacterium strains or the *Bifidobacterium* strains are sometimes referred to as "the lactic acid bacteria or the bacteria of *Bifidobacterium* of the invention", the "lactic acid bacterium strains or the *Bifidobacterium* strains of the invention" or simply strain SBT2687, strain SBT2651, strain SBT11178, strain SBT0320, strain SBT2785 and strain SBT2992 below.

The lactic acid bacterium strains were deposited on Dec. 1, 2020 or Jan. 19, 2021 to NITE Patent Microorganisms Depositary, National Institute of Technology and Evaluation (#122, 2-5-8 Kazusakamatari, Kisarazu-shi, Chiba 292-0818) with accession numbers of NITE ABP-03331 for strain SBT2687, NITE P-03330 for strain SBT2651, NITE P-03333 for strain SBT11178, NITE P-03332 for strain SBT0320, NITE P-03328 for strain SBT2785 and NITE P-03364 for strain SBT2992.

The lactic acid bacteria or the bacterial of *Bifidobacterium* of the invention are not restricted to the deposited lactic acid bacterium strains or the deposited *Bifidobacterium* strains and may be substantially equivalent lactic acid bacterium strains or *Bifidobacterium* strains of the deposited lactic acid bacterium strains or the deposited *Bifidobacterium* strains. The substantially equivalent lactic acid bacterium strains or *Bifidobacterium* strains refer to lactic acid bacterium strains or *Bifidobacterium* strains which belong to *Lactobacillus acidophilus, Lactobacillus helveticus, Lactobacillus salivarius, Lactobacillus salivarius* subsp. *salivarius, Lactococcus lactis* subsp. *lactis, Lactococcus lactis* subsp. *cremoris, Lactococcus laudensis, Streptococcus oralis, Bifidobacterium longum, Bifidobacterium longum* subsp. *infantis, Bifidobacterium pseudolongum* or *Bifidobacterium thermophilum* and which have a high joint function-improving action comparable to those of the deposited lactic acid bacterium strains or the deposited *Bifidobacterium* strains. The "lactic acid bacterium strains or *Bifidobacterium* strains which have a high joint function-improving action comparable to those of the deposited lactic acid bacterium strains or the deposited *Bifidobacterium* strains" mean, for example, lactic acid bacterium strains or *Bifidobacterium* strains having a chondrocyte growth-promoting effect measured by the following procedures 1) to 3) or an effect of suppressing the production of an inflammation factor, a cartilage matrix degradation factor, a pain factor or a neuronal outgrowth factor by synoviocytes measured by the procedures 4) to 7) which does not significantly differ from the chondrocyte growth-promoting effects or the effects of suppressing the production of an inflammation factor, a cartilage matrix degradation factor, a pain factor or a neuronal outgrowth factor by synoviocytes of the respective deposited lactic acid bacterium strains or the respective deposited *Bifidobacterium* strains.

(Evaluation Method of Chondrocyte Growth-Promoting Effect)

1) A mouse-derived cartilage precursor cell line (ATDC5) is seeded to a 96-well flat cell culture plate at 5,000 cells/well and cultured in a 5% (v/v) fetal bovine serum-containing Dulbecco's modified Eagle medium/Ham's F-12 mixture medium for 24 hours.

2) After removing all the medium, the medium is changed to a fetal bovine serum-free Dulbecco's modified Eagle medium/Ham's F-12 mixture medium, and each lactic acid bacterium cell homogenate or a *Bifidobacterium* cell homogenate is added to the medium at a final concentration of 0.1 mg/ml. The cells are further cultured for 48 hours.

3) After adding a cell growth reagent and culturing for five hours, the absorbance at 440 nm is measured. As the cell growth reagent, for example, WST-1 (Roche Diagnostics K.K.) can be used.

(Effect of Suppressing Production of Inflammation Factor, Cartilage Matrix Degradation Factor, Pain Factor or Neuronal Outgrowth Factor by Synoviocytes)

4) A human synovial membrane-derived cell line (SW982) is seeded to a 12-well flat cell culture plate at 100,000 cells/well and cultured in 10% (v/v) fetal bovine serum-containing Leibovitz's L-15 medium for a week.

5) After removing all the medium, the medium is changed to fetal bovine serum-free Leibovitz's L-15 medium, and human-IL-1β (Interleukin-1β) is added to the medium at a final concentration of 1 ng/ml. A lactic acid bacterium cell homogenate or a *Bifidobacterium* cell homogenate is added to the medium at a final concentration of 1 mg/ml, and the cells are further cultured for 24 hours.

6) All the medium is removed, and the total RNA is extracted using a reagent for total RNA extraction from a biological sample. Reverse transcription is conducted using a real-time PCR reverse transcription kit. As the reagent for total RNA extraction from a biological sample, for example, Sepasol RNA 1 SuperG reagent (manufactured by Nacalai Tesque, Inc.) can be used. As the real-time PCR reverse transcription kit, for example, ReverTra Ace qPCR RT Master Mix (manufactured by Toyobo Co., Ltd.) can be used.

7) Using the obtained cDNA, real-time PCR is conducted using a Realtime PCR reagent containing Taq DNA polymerase, and the expression levels of TNF-α (Tumor Necrosis Factor-α), MMP-13 (Matrix Metalloproteinase-13), COX-2 (Cyclooxygenase-2) and NGF (Nerve Growth Factor) genes are quantified. As the Realtime PCR reagent containing Taq DNA polymerase, for example, THUNDERBIRD qPCR Mix (manufactured by Toyobo Co., Ltd.) can be used.

When the chondrocyte growth-promoting effects are evaluated by the procedures 1) to 3), the measured cell growth-promoting effects of the lactic acid bacteria or the bacterial of *Bifidobacterium* of the invention are preferably 1.5 times or more, further preferably 2 times or more higher than the chondrocyte growth-promoting effect of the control without the addition of the lactic acid bacterium strains or the *Bifidobacterium* strains. The "measured cell growth-promoting effects" mean the magnitude of values of absorbance measured after the procedures 1) to 3).

Moreover, when the effects of suppressing the production of an inflammation factor, a cartilage matrix degradation factor, a pain factor or a neuronal outgrowth factor by synoviocytes are evaluated by the procedures 4) to 7), the measured effects of suppressing the production of the inflammation factor, the cartilage matrix degradation factor, the pain factor or the neuronal outgrowth factor by synoviocytes of the lactic acid bacteria or the bacterial of *Bifidobacterium* of the invention are preferably 1.5 times or more, further preferably 2 times or more, more preferably 3 times or more higher than the effect of suppressing the production of the inflammation factor, the cartilage matrix degradation factor, the pain factor or the neuronal outgrowth factor by synoviocytes of the control without the addition of the lactic acid bacterium strains or the *Bifidobacterium* strains. The "measured effects of suppressing the production of the inflammation factor, the cartilage matrix degradation factor, the pain factor or the neuronal outgrowth factor by synoviocytes" mean the expression levels measured after the procedures 4) to 7). As the expression level is lower, the effect of suppressing the production of the inflammation factor, the cartilage matrix degradation factor, the pain factor or the neuronal outgrowth factor by synoviocytes is greater. For example, in Test Example 2, *Lactococcus lactis* subsp. *lactis* strain SBT0625 had the inflammation factor at one fifth or less of that of the control (PBS) and thus has an inflammation-suppressing effect which is five times or more higher than the effect of the control.

In this regard, the evaluation methods are not limited to the above evaluation methods, and the chondrocyte growth-promoting effect or the effect of suppressing the production of an inflammation factor, a cartilage matrix degradation factor, a pain factor or a neuronal outgrowth factor by synoviocytes can be evaluated using a method for evaluating the chondrocyte growth-promoting effect or a method for evaluating the effect of suppressing the production of an inflammation factor, a cartilage matrix degradation factor, a pain factor or a neuronal outgrowth factor by synoviocytes which is known to one skilled in the art.

Moreover, the substantially equivalent lactic acid bacterium strains or *Bifidobacterium* strains have a nucleotide sequence of 16S ribosomal RNA gene having a homology of 98% or more, preferably 99% or more, more preferably 100% to the nucleotide sequence of 16S ribosomal RNA gene of the deposited lactic acid bacterium strains or the deposited *Bifidobacterium* strains and preferably have the identical bacteriological properties to those of the deposited lactic acid bacterium strains or the deposited *Bifidobacterium* strains. Furthermore, the lactic acid bacteria or the bacteria of *Bifidobacterium* of the invention may be lactic acid bacterium strains or *Bifidobacterium* strains which are bred from the deposited lactic acid bacterium strains, the deposited *Bifidobacterium* strains or substantially equivalent lactic acid bacterium strains or *Bifidobacterium* strains thereof by mutagenesis, gene recombination, selection of a naturally occurring mutant or the like, as long as the effects of the invention are not impaired.

(Intake Amount of Active Ingredient)

The intake amount of the bacterial cells or the culture of the lactic acid bacterium or the bacteria of *Bifidobacterium* of the invention is not particularly restricted as long as a joint function-improving action through an action of promoting growth of chondrocytes or an action of suppressing the production of an inflammation factor, a cartilage matrix degradation factor, a pain factor or a neuronal outgrowth factor by synoviocytes is exhibited with the amount, and the intake amount may be appropriately adjusted according to the easiness of production or a preferable daily intake amount. The subject of administration of the invention is not particularly limited, and although administration to a human is possible, the subject of administration may also be a non-human animal (for example, a dog, a cat, a horse, a cow, a rabbit or the like). When the subject of administration is a human, administration to a minor under the age of 20, an adult, a man, a woman, an elderly person at the age of 65 or older or the like is possible. The intake amount of the bacterial cells or the culture of the lactic acid bacterium or the bacteria of *Bifidobacterium* of the invention is determined individually considering the symptoms, the age, the gender and the like of the subject of administration, but in the case of an adult, the amount or the like may be generally adjusted in such a manner that the subject can take 10 to 200 g of the culture or the like of the lactic acid bacterium or the bacteria of *Bifidobacterium* or 0.1 to 5,000 mg of bacterial cells thereof. The bacterial cells or the culture of the lactic acid bacterium or the bacteria of *Bifidobacterium* of the invention may be orally taken directly, but when the bacterial cells or the culture is blended in a food or a drink, a nutritional composition, feed, an oral medicine or the like, the blending amount may be adjusted to achieve the intake amount. Through intake in this manner, a desired effect can be exhibited.

The subject of administration may be a patient with various arthropathies such as osteoarthritis including knee osteoarthritis as a typical example and rheumatoid arthritis or can also be a subject with a high risk of morbidity or a healthy subject without the disease.

(Regarding Use Method of Lactic Acid Bacterium or Bacteria of *Bifidobacterium* of Invention for Foor or Drink and Pharmaceutical Agent)

The bacterial cells or the culture of the lactic acid bacterium or the bacteria of *Bifidobacterium* of the invention may be directly used as a joint function-improving composition individually or in any combination but can also be formulated before use into powder, granules, tablets, capsules, a drink or the like according to a general method, according to the need, within the range in which the joint function-improving action through the action of promoting growth of chondrocytes or the action of suppressing the production of an inflammation factor, a cartilage matrix degradation factor, a pain factor or a neuronal outgrowth factor by synoviocytes is not lost. Moreover, the bacterial cells or the culture can also be blended, directly or after formulation, in a food or a drink such as a nutrient, powdered milk, a milk beverage, a lactic acid bacteria beverage, fermented milk, a soft drink, cheese, margarin, cream, pudding, jelly and wafer, as well as in a nutritional composition, feed and a pharmaceutical agent.

The bacterial cells or the culture of the lactic acid bacterium or the bacteria of *Bifidobacterium* of the invention can be used with a raw material which is generally contained in other foods or drinks, feed and medicines, such as stabilizers, saccharides, lipids, flavors, vitamins, minerals, flavonoids and polyphenols.

The food or the drink of the invention can also be used as a food with a function claim, a food for a specified health use, a food with a nutrient function claim or a cosmetic food.

For the formulation, a diluent or an excipient which is generally used, such as a filler, an expander, a binder, a disintegrating agent, a surfactant and a lubricant, can be used. As the excipient, for example, one kind of or a combination of two kinds or more of sucrose, lactose, starch, crystalline cellulose, mannitol, light silicic anhydride, magnesium aluminate, synthetic aluminum silicate, magnesium aluminometasilicate, calcium carbonate, sodium hydrogen carbonate, calcium hydrogen phosphate, carboxylmethylcellulose calcium and the like can be added.

The invention will be explained in detail below referring to Examples and Test Examples, but the invention is not limited by the Examples and the Test Examples. In the present specification, % is % by mass unless otherwise specifically noted.

EXAMPLES

Example 1

*Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670 and *Streptococcus oralis* strain SBT0320 were individually cultured at 37° C. for 16 hours for three generations or more in MRS broth (manufactured by DIFCO) which was sterilized at 121° C. for 15 minutes, and the strains were thus activated. The cultures were each seeded to the same medium at 3% (v/v) and cultured at 37° C. for 16 hours, and then the bacterial cells were isolated by centrifugation. The bacterial cells were washed twice with sterile saline and once with ultra-pure water and then lyophilized, and thus bacterial cells of *Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670 and *Streptococcus oralis* strain SBT0320 were obtained (Example products 1). Thus obtained bacterial cells of *Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670 and *Streptococcus oralis* strain SBT0320 can be directly used as the lactic acid bacteria having a joint function-improving action of the invention. The bacterial cells of the Example products 1 were physically homogenized using easy beads (AMR Inc.) and used for the following tests.

Example 2

*Lactococcus lactis* subsp. *lactis* strain SBT0625, *Lactococcus lactis* subsp. *cremoris* strain SBT11373 and *Lactococcus laudensis* strain SBT11178 were individually cultured at 30° C. for 16 hours to 24 hours for three generations or more in a medium obtained by adding a lactose solution which was sterilized at 121° C. for 15 minutes at a final concentration of 0.5% to M17 medium (manufactured by DIFCO) which was sterilized at 121° C. for 15 minutes, and the strains were thus activated. The cultures were each seeded to the same medium at 3% (v/v) and cultured at 30° C. for 16 hours to 24 hours, and then the bacterial cells were isolated by centrifugation. The bacterial cells were washed twice with sterile saline and once with ultra-pure water and then lyophilized, and thus bacterial cells of *Lactococcus lactis* subsp. *lactis* strain SBT0625, *Lactococcus lactis* subsp. *cremoris* strain SBT11373 and *Lactococcus laudensis* strain SBT11178 were obtained (Example products 2). Thus obtained bacterial cells of *Lactococcus lactis* subsp. *lactis* strain SBT0625, *Lactococcus lactis* subsp. *cremoris* strain SBT11373 and *Lactococcus laudensis* strain SBT11178 can be directly used as the lactic acid bacteria having a joint function-improving action of the invention. The bacterial cells of the Example products 2 were physically homogenized using easy beads (AMR Inc.) and used for the following tests.

Example 3

Bifidobacterium longum strain SBT2928, Bifidobacterium longum subsp. infantis strain SBT2785, Bifidobacterium pseudolongum strain SBT2922 and Bifidobacterium thermophilum strain SBT2992 were individually cultured at 37° C. for 16 hours to 21 hours for three generations or more in a medium obtained by adding a glucose solution which was sterilized at 115° C. for 15 minutes at a final concentration of 1% to GAM medium (manufactured by Nissui Pharmaceutical Co., Ltd.) which was sterilized at 115° C. for 15 minutes, and the strains were thus activated. The cultures were each seeded to the same medium at 3% (v/v) and cultured at 37° C. for 16 hours to 21 hours, and then the bacterial cells were isolated by centrifugation. The bacterial cells were washed twice with sterile saline and once with ultra-pure water and then lyophilized, and thus bacterial cells of Bifidobacterium longum strain SBT2928, Bifidobacterium longum subsp. infantis strain SBT2785, Bifidobacterium pseudolongum strain SBT2922 and Bifidobacterium thermophilum strain SBT2992 were obtained (Example products 3). Thus obtained bacterial cells of Bifidobacterium longum strain SBT2928, Bifidobacterium longum subsp. infantis strain SBT2785, Bifidobacterium pseudolongum strain SBT2922 and Bifidobacterium thermophilum strain SBT2992 can be directly used as the bacteria of Bifidobacterium having a joint function-improving action of the invention. The bacterial cells of the Example products 3 were physically homogenized using easy beads (AMR Inc.) and used for the following tests.

Comparative Example 1

Weissella confusa strain No. 1 possessed by Megmilk Snow Brand Co., Ltd. was cultured at 37° C. for 16 hours for three generations or more in MRS broth (manufactured by DIFCO) which was sterilized at 121° C. for 15 minutes, and the strain was thus activated. The culture was seeded to the same medium at 3% (v/v) and cultured at 37° C. for 16 hours, and then the bacterial cells were isolated by centrifugation. The bacterial cells were washed twice with sterile saline and once with ultra-pure water and then lyophilized, and bacterial cells of Weissella confusa strain No. 1 were thus obtained (Comparative Example product 1). The bacterial cells of the Comparative Example product 1 were physically homogenized using easy beads (AMR Inc.) and used for the following tests.

Comparative Example 2

Pediococcus pentosaceus strain No. 1 possessed by Megmilk Snow Brand Co., Ltd. was cultured at 37° C. for 16 hours for three generations or more in MRS broth (manufactured by DIFCO) which was sterilized at 121° C. for 15 minutes, and the strain was thus activated. The culture was seeded to the same medium at 3% (v/v) and cultured at 37° C. for 16 hours, and then the bacterial cells were isolated by centrifugation. The bacterial cells were washed twice with sterile saline and once with ultra-pure water and then lyophilized, and bacterial cells of Pediococcus pentosaceus strain No. 1 were thus obtained (Comparative Example product 2). The bacterial cells of the Comparative Example product 2 were physically homogenized using easy beads (AMR Inc.) and used for the following tests.

Comparative Example 3

Leuconostoc mesenteroides strain No. 1 possessed by Megmilk Snow Brand Co., Ltd. was cultured at 25° C. for 24 hours for three generations or more in MRS broth (manufactured by DIFCO) which was sterilized at 121° C. for 15 minutes, and the strain was thus activated. The culture was seeded to the same medium at 3% (v/v) and cultured at 25° C. for 24 hours, and then the bacterial cells were isolated by centrifugation. The bacterial cells were washed twice with sterile saline and once with ultra-pure water and then lyophilized, and bacterial cells of Leuconostoc mesenteroides strain No. 1 were thus obtained (Comparative Example product 3). The bacterial cells of the Comparative Example product 3 were physically homogenized using easy beads (AMR Inc.) and used for the following tests.

Test Example 1

The chondrocyte growth-promoting effect of the bacterial cell homogenate of Bifidobacterium thermophilum strain SBT2992 of the Example product 3 was examined. For comparison, the chondrocyte growth-promoting effect of the bacterial cell homogenate of Weissella confusa strain No. 1 of the Comparative Example product 1 was also examined.

A mouse-derived cartilage precursor cell line (ATDC5) was seeded to a 96-well flat cell culture plate at 5,000 cells/well and cultured in a 5% (v/v) fetal bovine serum-containing Dulbecco's modified Eagle medium/Ham's F-12 mixture medium at 37° C. in an environment of 5% $CO_2$ for 24 hours. Then, all the medium was removed, and the cells were washed with fetal bovine serum-free Dulbecco's modified Eagle medium/Ham's F-12 medium. The medium was changed, and the bacterial cell homogenates of Bifidobacterium thermophilum strain SBT2992 of the Example product 3 and Weissella confusa strain No. 1 of the Comparative Example product 1 were added to the medium at a final concentration of 0.1 mg/ml. The cells were cultured for 48 hours. Then, all the medium was removed, and after a cell growth reagent WST-1 (Roche Diagnostics K.K.) was added in such a manner that one tenth of the amount was contained in the medium, the cells were cultured for five hours. The absorbances at 440 nm were measured using a plate reader. Because WST-1 is reduced to a formazan dye by metabolic activity of living cells, the formazan dye amount is in proportion to the number of cells having metabolic activity. Thus, the absorbance values reflecting the formazan dye amounts were used as indexes of the chondrocyte growth-promoting effect.

TABLE 1

| Bacterial Strain Name | Absorbance (440 nm) |
|---|---|
| Control (PBS) | 0.626 ± 0.021 |
| Weissella confusa strain No. 1 | 0.632 ± 0.038 |
| Bifidobacterium thermophilum strain SBT2992 | 1.269 ± 0.029 ✕ |

The values are the averages ± standard deviations (n = 4).
✕ shows a significant difference (p < 0.05) from the control (PBS).

As a result, when the bacterial cell homogenate of Bifidobacterium thermophilum strain SBT2992 was added, the cell count of the cartilage precursor cells increased significantly compared to that of the control (PBS). It was thus found that the bacterial cell homogenate of *Bifidobacterium thermophilum* strain SBT2992 of the invention has a growth promotion effect on chondrocytes. On the other hand, the bacterial cell homogenate of *Weissella confusa* strain No. 1 of the Comparative Example product 1 did not show the growth promotion effect on chondrocytes.

Test Example 2

The effects of suppressing the production of an inflammation factor by synoviocytes of the bacterial cell homogenates of *Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670 and *Streptococcus oralis* strain SBT0320 of the Example products 1, *Lactococcus lactis* subsp. *lactis* strain SBT0625, *Lactococcus lactis* subsp. *cremoris* strain SBT11373 and *Lactococcus laudensis* strain SBT11178 of the Example products 2 and *Bifidobacterium longum* strain SBT2928 and *Bifidobacterium thermophilum* strain SBT2992 of the Example products 3 were examined. For comparison, the effect of suppressing the production of an inflammation factor by synoviocytes of the bacterial cell homogenate of *Pediococcus pentosaceus* strain No. 1 of the Comparative Example product 2 was also examined.

A human synovial membrane-derived cell line (SW982) was seeded to 12-well flat cell culture plates at 100,000 cells/well and cultured in 10% (v/v) fetal bovine serum-containing Leibovitz's L-15 medium at 37° C. in an environment of 5% $CO_2$ for a week. Then, all the medium was removed, and the cells were washed with fetal bovine serum-free Leibovitz's L-15 medium. The medium was changed. Human-IL-1β (Interleukin-1β) was added to the medium at a final concentration of 1 ng/ml, and the bacterial cell homogenates of the invention were added to the medium at a final concentration of 1 mg/ml. The cells were further cultured for 24 hours. Then, the total RNA was extracted from the cultured cells using Sepasol RNA 1 SuperG reagent (manufactured by Nacalai Tesque, Inc.). ReverTra Ace qPCR RT Master Mix (manufactured by Toyobo Co., Ltd.) was used for the reverse transcription. Real-time PCR was conducted with THUNDERBIRD qPCR Mix (manufactured by Toyobo Co., Ltd.) using the obtained cDNA, and thus the gene expression levels of an inflammation factor, TNF-α (Tumor Necrosis Factor-α), were quantified. Here, the expression levels of GAPDH (Glyceraldehyde-3-phosphate dehydrogenase) gene were used as an internal standard for evaluating the gene expression levels. For the analysis, the primers of SEQ ID NOs: 1 and 2 of the sequence listing were used for TNF-α, and the primers of SEQ ID NOs: 3 and 4 of the sequence listing were used for GAPDH.

TABLE 2

| SEQ ID NO: | | Nucleotide Sequence (5' = 3') |
| --- | --- | --- |
| 1 | Forward | GAG GCC AAG CCC TGG TAT G |
| 2 | Reverse | CGG GCC GAT TGA TCT CAG C |
| 3 | Forward | CTG GGC TAC ACT GAG CAC C |
| 4 | Reverse | AAG TGG TCG TTG AGG GCA ATG |

TABLE 3

| Relative TNF-@ Gene Expression Level | |
| --- | --- |
| Bacterial Strain Name | Relative TNF-α Gene Expression Level |
| Control (PBS) | 100.0 ± 11.5 |
| *Pediococcus pentosacaus* strain No. 1 | 91.6 ± 20.7 |
| *Lactobacillus acidophilus* strain SBT2062 | 45.2 ± 2.6 X |
| *Lactobacillus helveticus* strain SBT2161 | 32.1 ± 2.3 X |
| *Lactobacillus helveticus* strain SBT2171 | 40.4 ± 1.2 X |
| *Lactobacillus salivarius* strain SBT2687 | 6.3 ± 2.9 X |
| *Lactobacillus salivarius* strain SBT2651 | 10.4 ± 9.9 X |
| *Lactobacillus salivarius* subsp. *salivarius* strain SBT2670 | 15.4 ± 17.5 X |
| *Streptococcus oralis* strain SBT0320 | 25.5 ± 1.2 X |
| *Lactococcus lactis* subsp. *lactis* strain SBT0625 | 18.7 ± 10.6 X |
| *Lactococcus lactis* subsp. *cremoris* strain SBT11373 | 22.6 ± 0.8 X |
| *Lactococcus laudensis* strain SBT11178 | 17.9 ± 1.3 X |
| *Bifidobacterium longum* strain SBT2928 | 28.5 ± 11.5 X |
| *Bifidobacter ium thermophilum* strain SBT2992 | 21.7 ± 0.6 X |

The values are the averages ± standard deviations (n = 3).
X shows a significant difference (p < 0.05) from the control (PBS).

As a result, when the bacterial cell homogenates of *Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670, *Streptococcus oralis* strain SBT0320, *Lactococcus lactis* subsp. *lactis* strain SBT0625, *Lactococcus lactis* subsp. *cremoris* strain SBT11373, *Lactococcus laudensis* strain SBT11178, *Bifidobacterium longum* strain SBT2928 and *Bifidobacterium thermophilum* strain SBT2992 were added, the expression of TNF-α gene in synoviocytes was suppressed significantly compared to that of the control (PBS) in all the cases. Thus, it was found that the bacterial cell homogenates of *Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670, *Streptococcus oralis* strain SBT0320, *Lactococcus lactis* subsp. *lactis* strain SBT0625, *Lactococcus lactis* subsp. *cremoris* strain SBT11373, *Lactococcus laudensis* strain SBT11178, *Bifidobacterium longum* strain SBT2928 and *Bifidobacterium thermophilum* strain SBT2992 of the invention have an effect of suppressing the production of an inflammation factor by synoviocytes. On the other hand, the bacterial cell homogenate of *Pediococcus pentosaceus* strain No. 1 of the Comparative Example product 2 did not show the effect of suppressing the production of an inflammation factor by synoviocytes.

Test Example 3

The effects of suppressing the production of a cartilage matrix degradation factor by synoviocytes of the bacterial cell homogenates of *Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670 and *Streptococcus oralis* strain SBT0320 of the Example products 1, *Lactococcus lactis* subsp. *lactis* strain SBT0625, *Lactococcus lactis* subsp. *cremoris* strain SBT11373 and *Lactococcus laudensis* strain SBT11178 of the Example products 2 and *Bifidobacterium longum* strain SBT2928, *Bifidobacterium longum* subsp. *infantis* strain SBT2785 and *Bifidobacterium pseudolongum* strain SBT2922 of the Example products 3 were examined. For comparison, the effect of suppressing the production of a cartilage matrix degradation factor by synoviocytes of the bacterial cell homogenate of *Leuconostoc mesenteroides* strain No. 1 of the Comparative Example product 3 was also examined.

A human synovial membrane-derived cell line (SW982) was seeded to 12-well flat cell culture plates at 100,000 cells/well and cultured in 10% (v/v) fetal bovine serum-containing Leibovitz's L-15 medium at 37° C. in an environment of 5% $CO_2$ for a week. Then, all the medium was removed, and the cells were washed with fetal bovine serum-free Leibovitz's L-15 medium. The medium was changed. Human-IL-1β (Interleukin-1β) was added to the medium at a final concentration of 1 ng/ml, and the bacterial cell homogenates of the invention were added to the medium at a final concentration of 1 mg/ml. The cells were further cultured for 24 hours. Then, the total RNA was extracted from the cultured cells using Sepasol RNA 1 SuperG reagent (manufactured by Nacalai Tesque, Inc.). ReverTraAce qPCR RT Master Mix (manufactured by Toyobo Co., Ltd.) was used for the reverse transcription. Real-time PCR was conducted with THUNDERBIRD qPCR Mix (manufactured by Toyobo Co., Ltd.) using the obtained cDNA, and thus the gene expression levels of a cartilage matrix degradation factor, MMP-13 (Matrix Metalloproteinase-13), were quantified. Here, the expression levels of GAPDH (Glyceraldehyde-3-phosphate dehydrogenase) gene were used as an internal standard for evaluating the gene expression levels. For the analysis, the primers of SEQ ID NOs: 5 and 6 of the sequence listing were used for MMP-13, and the primers of SEQ ID NOs: 3 and 4 of the sequence listing were used for GAPDH.

TABLE 4

| SEQ ID NO: | | Nucleotide Sequence (5' = 3') |
|---|---|---|
| 5 | Forward | TCC TGA TGT GGG TGA ATA CAA TG |
| 6 | Reverse | GCC ATC GTG AAG TCT GGT AAA AT |
| 3 | Forward | CTG GGC TAC ACT GAG CAC C |
| 4 | Reverse | AAG TGG TCG TTG AGG GCA ATG |

TABLE 5

Relative MMP-13 Gene Expression Level

| Bacterial Strain Name | Relative MMP-13 Gene Expression Level |
|---|---|
| Control (PBS) | 100.0 ± 41.5 |
| *Leuconostoc mesenteroides* strain No. 1 | 83.7 ± 26.2 |
| *Lactobacillus acidophilus* strain SBT2062 | 32.7 ± 14.0 ✕ |
| *Lactobacillus helveticus* strain SBT2161 | 43.6 ± 13.0 ✕ |

TABLE 5-continued

Relative MMP-13 Gene Expression Level

| Bacterial Strain Name | Relative MMP-13 Gene Expression Level |
|---|---|
| *Lactobacillus helveticus* strain SBT2171 | 42.3 ± 11.4 ✕ |
| *Lactobacillus salivarius* strain SBT2687 | 11.0 ± 2.6 ✕ |
| *Lactobacillus salivarius* strain SBT2651 | 22.0 ± 4.0 ✕ |
| *Lactobacillus salivarius* subsp. *salivar* strain SBT2670 | 15.1 ± 14.1 ✕ |
| *Streptococcus oralis* strain SBT0320 | 24.3 ± 11.5 ✕ |
| *Lactococcus lactis* subsp. *lactis* strain SBT0625 | 40.6 ± 13.9 ✕ |
| *Lactococcus lactis* subsp. *cremoris* strain SBT11373 | 24.3 ± 5.6 ✕ |
| *Lactococcus laudensis* strain SBT11178 | 13.8 ± 3.9 ✕ |
| *Bifidobacterium longum* strain SBT2928 | 30.6 ± 8.9 ✕ |
| *Bifidobacterium longum* subsp. *infantis* strain SBT2785 | 36.7 ± 6.8 ✕ |
| *Bifidobacterium pseudolongum* strain SBT2922 | 22.7 ± 15.2 ✕ |

The values are the averages ± standard deviations (n = 3).
✕ shows a significant difference ($p < 0.05$) from the control (PBS).

As a result, when the bacterial cell homogenates of *Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670, *Streptococcus oralis* strain SBT0320, *Lactococcus lactis* subsp. *lactis* strain SBT0625, *Lactococcus lactis* subsp. *cremoris* strain SBT11373, *Lactococcus laudensis* strain SBT11178, *Bifidobacterium longum* strain SBT2928, *Bifidobacterium longum* subsp. *infantis* strain SBT2785 and *Bifidobacterium pseudolongum* strain SBT2922 were added, the expression of MMP-13 gene in synoviocytes was suppressed significantly compared to that of the control (PBS) in all the cases. Thus, it was found that the bacterial cell homogenates of *Lactobacillus acidophilus* strain SBT2062, *Lactobacillus helveticus* strain SBT2161 and strain SBT2171, *Lactobacillus salivarius* strain SBT2687 and strain SBT2651, *Lactobacillus salivarius* subsp. *salivarius* strain SBT2670, *Streptococcus oralis* strain SBT0320, *Lactococcus lactis* subsp. *lactis* strain SBT0625, *Lactococcus lactis* subsp. *cremoris* strain SBT11373, *Lactococcus laudensis* strain SBT11178, *Bifidobacterium longum* strain SBT2928, *Bifidobacterium longum* subsp. *infantis* strain SBT2785 and *Bifidobacterium pseudolongum* strain SBT2922 of the invention have an effect of suppressing the production of a cartilage matrix degradation factor by synoviocytes. On the other hand, the bacterial cell homogenate of *Leuconostoc mesenteroides* strain No. 1 of the Comparative Example product 3 did not show the effect of suppressing the production of a cartilage matrix degradation factor by synoviocytes.

Test Example 4

The effects of suppressing the production of a pain factor by synoviocytes of the bacterial cell homogenates of *Lactobacillus salivarius* strain SBT2687 of the Example product 1 and *Bifidobacterium longum* subsp. *infantis* strain SBT2785 and *Bifidobacterium pseudolongum* strain SBT2922 of the Example products 3 were examined. For comparison, the effect of suppressing the production of a pain factor by synoviocytes of the bacterial cell homogenate of *Weissella confusa* strain No. 1 of the Comparative Example product 1 was also examined.

A human synovial membrane-derived cell line (SW982) was seeded to 12-well flat cell culture plates at 100,000 cells/well and cultured in 10% (v/v) fetal bovine serum-containing Leibovitz's L-15 medium at 37° C. in an environment of 5% $CO_2$ for a week. Then, all the medium was removed, and the cells were washed with fetal bovine serum-free Leibovitz's L-15 medium. The medium was changed. Human-IL-1β (Interleukin-1β) was added to the medium at a final concentration of 1 ng/ml, and the bacterial cell homogenates of the invention were added to the medium at a final concentration of 1 mg/ml. The cells were further cultured for 24 hours. Then, the total RNA was extracted from the cultured cells using Sepasol RNA 1 SuperG reagent (manufactured by Nacalai Tesque, Inc.). ReverTra Ace qPCR RT Master Mix (manufactured by Toyobo Co., Ltd.) was used for the reverse transcription. Real-time PCR was conducted with THUNDERBIRD qPCR Mix (manufactured by Toyobo Co., Ltd.) using the obtained cDNA, and thus the gene expression levels of a pain factor, COX-2 (Cyclooxygenase-2), were quantified. Here, the expression levels of GAPDH (Glyceraldehyde-3-phosphate dehydrogenase) gene were used as an internal standard for evaluating the gene expression levels. For the analysis, the primers of SEQ ID NOs: 7 and 8 of the sequence listing were used for COX-2, and the primers of SEQ ID NOs: 3 and 4 of the sequence listing were used for GAPDH.

TABLE 6

| SEQ ID NO: | | Nucleotide Sequence (5' = 3') |
|---|---|---|
| 7 | Forward | ATG CTG ACT ATG GCT ACA AAA GC |
| 8 | Reverse | TCG GGC AAT CAT CAG GCA C |
| 3 | Forward | CTG GGC TAC ACT GAG CAC C |
| 4 | Reverse | AAG TGG TCG TTG AGG GCA ATG |

TABLE 7

Relative COX-2 Gene Expression Level

| Bacterial Strain Name | Relative COX-2 Gene Expression Level |
|---|---|
| Control (PBS) | 100.0 ± 20.0 ✕ |
| *Weissella confusa* strain No. 1 | 118.0 ± 31.8 ✕ |
| *Lactobacillus salivarius* strain SBT2687 | 28.6 ± 24.0 ✕ |
| *Bifidobacterium longum* subsp. *infantis* strain SBT2785 | 35.7 ± 15.8 ✕ |
| *Bifidobacterium pseudolongum* strain SBT2922 | 48.7 ± 9.3 ✕ |

The values are the averages ± standard deviations (n = 3).
✕ shows a significant difference (p < 0.05) from the control (PBS).

As a result, when the bacterial cell homogenates of *Lactobacillus salivarius* strain SBT2687, *Bifidobacterium longum* subsp. *infantis* strain SBT2785 and *Bifidobacterium pseudolongum* strain SBT2922 were added, the expression of COX-2 gene in synoviocytes was suppressed significantly compared to that of the control (PBS) in all the cases. Thus, it was found that the bacterial cell homogenates of *Lactobacillus salivarius* strain SBT2687, *Bifidobacterium longum* subsp. *infantis* strain SBT2785 and *Bifidobacterium pseudo-*

*longum* strain SBT2922 of the invention have an effect of suppressing the production of a pain factor by synoviocytes. On the other hand, the bacterial cell homogenate of *Weissella confusa* strain No. 1 of the Comparative Example product 1 did not show the effect of suppressing the production of a pain factor by synoviocytes.

Test Example 5

The effects of suppressing the production of a neuronal outgrowth factor by synoviocytes of the bacterial cell homogenates of *Lactobacillus salivarius* strain SBT2687 and strain SBT2651 of the Example products 1 and *Bifidobacterium longum* subsp. *infantis* strain SBT2785 and *Bifidobacterium pseudolongum* strain SBT2922 of the Example products 3 were examined. For comparison, the effect of suppressing the production of a neuronal outgrowth factor by synoviocytes of the bacterial cell homogenate of *Pediococcus pentosaceus* strain No. 1 of the Comparative Example product 2 was also examined.

A human synovial membrane-derived cell line (SW982) was seeded to 12-well flat cell culture plates at 100,000 cells/well and cultured in 10% (v/v) fetal bovine serum-containing Leibovitz's L-15 medium at 37° C. in an environment of 5% $CO_2$ for a week. Then, all the medium was removed, and the cells were washed with fetal bovine serum-free Leibovitz's L-15 medium. The medium was changed. Human-IL-1β (Interleukin-1β) was added to the medium at a final concentration of 1 ng/ml, and the bacterial cell homogenates of the invention were added to the medium at a final concentration of 1 mg/ml. The cells were further cultured for 24 hours. Then, the total RNA was extracted from the cultured cells using Sepasol RNA 1 SuperG reagent (manufactured by Nacalai Tesque, Inc.). ReverTra Ace qPCR RT Master Mix (manufactured by Toyobo Co., Ltd.) was used for the reverse transcription. Real-time PCR was conducted with THUNDERBIRD qPCR Mix (manufactured by Toyobo Co., Ltd.) using the obtained cDNA, and thus the gene expression levels of a neuronal outgrowth factor, NGF (Nerve Growth Factor), were quantified. Here, the expression levels of GAPDH (Glyceraldehyde-3-phosphate dehydrogenase) gene were used as an internal standard for evaluating the gene expression levels. For the analysis, the primers of SEQ ID NOs: 9 and 10 of the sequence listing were used for NGF, and the primers of SEQ ID NOs: 3 and 4 of the sequence listing were used for GAPDH.

TABLE 8

| SEQ ID NO: | | Nucleotide Sequence (5' = 3') |
|---|---|---|
| 9 | Forward | GGC AGA CCC GCA ACA TTA CT |
| 10 | Reverse | CAC CAC CGA CCT CGA AGT C |
| 3 | Forward | CTG GGC TAC ACT GAG CAC C |
| 4 | Reverse | AAG TGG TCG TTG AGG GCA ATG |

TABLE 9

Relative NGF Gene Expression Level

| Bacterial Strain Name | Relative NGF Gene Expression Level |
|---|---|
| Control (PBS) | 100.0 ± 13.4 ✕ |
| *Pediococcus pentosaceus* | 94.3 ± 24.1 ✕ |

TABLE 9-continued

| Relative NGF Gene Expression Level | |
| --- | --- |
| Bacterial Strain Name | Relative NGF Gene Expression Level |
| strain No. 1 | |
| *Lactobacillus salivarius* strain SBT2687 | 23.6 ± 3.4 X |
| *Lactobacillus salivarius* strain SBT2651 | 38.1 ± 10.2 X |
| *Bifidobacterium longum* subsp. *infantis* strain SBT2785 | 17.8 ± 4.6 X |
| *Bifidobacterium pseudolongum* strain SBT2922 | 44.8 ± 12.7 X |

The values are the averages ± standard deviations (n = 3).
X shows a significant difference (p < 0.05) from the control (PBS).

As a result, when the bacterial cell homogenates of *Lactobacillus salivarius* strain SBT2687 and strain SBT2651, *Bifidobacterium longum* subsp. *infantis* strain SBT2785 and *Bifidobacterium pseudolongum* strain SBT2922 were added, the expression of NGF gene in synoviocytes was suppressed significantly compared to that of the control (PBS) in all the cases. Thus, it was found that the bacterial cell homogenates of *Lactobacillus salivarius* strain SBT2687 and strain SBT2651, *Bifidobacterium longum* subsp. *infantis* strain SBT2785 and *Bifidobacterium pseudolongum* strain SBT2922 of the invention have an effect of suppressing the production of a neuronal outgrowth factor by synoviocytes. On the other hand, the bacterial cell homogenate of *Pediococcus pentosaceus* strain No. 1 of the Comparative Example product 2 did not show the effect of suppressing the production of a neuronal outgrowth factor by synoviocytes.

Example 4

(Preparation of Joint Function-Improving Capsules)

Raw materials were mixed with the composition shown in Table 10, then granulated by a general method and packed in capsules, and thus joint function-improving capsules of the invention were produced.

TABLE 10

| | Weight (%) |
| --- | --- |
| Strain SBT2062 (Example product 1) | 0.1 |
| Lactose | 41.4 |
| Soluble Starch | 58.0 |
| Magnesium Stearate | 0.5 |

Example 5

(Preparation of Joint Function-Improving Tablets)

Raw materials were mixed with the composition shown in Table 11 and then formed and tableted in an amount of 1 g by a general method, and thus joint function-improving tablets of the invention were produced.

TABLE 11

| | Weight (%) |
| --- | --- |
| Hydrous Crystalline Glucose | 93.49 |
| Strain SBT2161 (Example product 1) | 0.01 |

TABLE 11-continued

| | Weight (%) |
| --- | --- |
| Mineral Mixture | 5.00 |
| Sugar Ester | 1.00 |
| Flavor | 0.50 |

Example 6

(Preparation of Joint Function-Improving Liquid Nutritional Composition)

The bacterial cells of strain SBT2171 (Example product 1) in an amount of 25 g were dissolved in 4975 g of deionized water, and after heating to 40° C., the solution was stirred and mixed with a TK homogenizing mixer (TK ROBO MICS; manufactured by Tokushu Kika Kogyo Co., Ltd.) at 6,000 rpm for 10 minutes. Thus, a 25 g/5 kg bacterial cell solution of strain SBT2171 was obtained. In 5.0 kg of the strain SBT2171 solution, 5.0 kg of casein, 5.0 kg of soy protein, 1.0 kg of fish oil, 3.0 kg of perilla oil, 17.0 kg of dextrin, 6.0 kg of a mineral mixture, 1.95 kg of a vitamin mixture, 2.0 kg of an emulsifier, 4.0 kg of a stabilizer and 0.05 kg of a flavor were blended, and the mixture was packed in 200-ml retort pouches and sterilized with a retort sterilizer (a type 1 pressure vessel, TYPE: RCS-4CRTGN, manufactured by Hisaka Works, Ltd.) at 121° C. for 20 minutes. Thus, 50 kg of a joint function-improving liquid nutritional composition of the invention was produced. Here, 100 mg of bacterial cells of strain SBT2171 were contained in 200 g of the joint function-improving liquid nutritional composition of the invention.

Example 7

(Preparation of Joint Function-Improving Drink)

After dissolving 0.5 g of the bacterial cells of strain SBT2687 of the Example product 1 in 699.5 g of deionized water, the solution was heated to 40° C. and then stirred and mixed with an ultra-disperser (ULTRA-TURRAX T-25; manufactured by IKA Japan) at 9,500 rpm for 20 minutes. After adding 100 g of maltitol, 2 g of an acidulant, 20 g of reduced water, 2 g of a flavor and 176 g of deionized water, the mixture was packed in 100-ml glass bottles, sterilized at 95° C. for 15 seconds and then sealed tightly, and thus 10 bottles (containing 100 ml) of a joint function-improving drink of the invention were prepared. Here, 50 mg of bacterial cells of strain SBT2687 were contained in 100 g of the joint function-improving drink of the invention.

Example 8

(Preparation of Joint Function-Improving Dog Food)

The bacterial cells of strain SBT2651 of the Example product 1 in an amount of 2 g were dissolved in 3,998 g of deionized water, and after heating to 40° C., the solution was stirred and mixed with a TK homogenizing mixer (type MARK II 160; manufactured by Tokushu Kika Kogyo Co., Ltd.) at 3,600 rpm for 20 minutes. Thus, a 2 g/4 kg bacterial cell solution of strain SBT2651 was obtained. In 2 kg of the bacterial cell solution of strain SBT2651, 1 kg of soybean cake, 1 kg of powdered skim milk, 0.4 kg of soybean oil, 0.2 kg of corn oil, 2.3 kg of palm oil, 1 kg of corn starch, 0.9 kg of flour, 0.2 kg of wheat bran, 0.5 kg of a vitamin mixture, 0.3 kg of cellulose and 0.2 kg of a mineral mixture were blended, and the mixture was heat-sterilized at 120° C. for four minutes. Thus, 10 kg of joint function-improving feed of the invention was produced. Here, 10 mg of bacterial cells of strain SBT2651 were contained in 100 g of the joint function-improving feed of the invention.

Example 9

(Preparation of Joint Function-Improving Powdered Milk)

The bacterial cells of strain SBT2670 of the Example product 1 in an amount of 2 g, 9.998 kg of powdered skim milk and 90 kg of deionized water were mixed, and after heating to 40° C., the mixture was stirred and mixed with a TK homogenizing mixer (TK ROBO MICS; manufactured by Tokushu Kika Kogyo Co., Ltd.) at 6,000 rpm for 10 minutes. The solution was spray-dried, and thus 10 kg of joint function-improving powdered milk of the invention was produced. Here, 2 mg of bacterial cells of strain SBT2670 were contained in 10 g of the joint function-improving powdered milk of the invention.

Example 10

(Preparation of Joint Function-Improving Milk Beverage)

The bacterial cells of strain SBT0625 of the Example product 2 in an amount of 1 g and 9.999 kg of cow's milk were mixed, and after heating to 40° C., the mixture was stirred and mixed with a TK homogenizing mixer (TK ROBO MICS; manufactured by Tokushu Kika Kogyo Co., Ltd.) at 6,000 rpm for 10 minutes. After heat sterilization at 130° C. for two seconds, the mixture was cooled to 10° C. or lower, and thus 10 kg of a joint function-improving milk beverage of the invention was produced. Here, 20 mg of bacterial cells of strain SBT0625 were contained in 200 g of the joint function-improving milk beverage of the invention.

Example 11

(Preparation of Joint Function-Improving Fermented Milk)

The bacterial cells of strain SBT11373 of the Example product 2 in an amount of 0.1 g, 1700 g of powdered skim milk, 300 g of glucose and 7699.9 g of deionized water were mixed, and the mixture was heat-sterilized by keeping at 95° C. for two hours. The mixture was cooled to 37° C., and 300 g of a lactic acid bacterium starter (*Streptococcus thermophilus*) was inoculated. After stirring and mixing, the mixture was fermented in an incubator kept at 37° C. until the pH reached 4.0. After the pH reached 4.0, the resultant was cooled to 10° C. or lower, and thus 10 kg of joint function-improving fermented milk of the invention was produced. Here, 2 mg of bacterial cells of strain SBT11373 were contained in 200 g of the joint function-improving fermented milk of the invention.

Example 12

(Preparation of Joint Function-Improving Lactic Acid Bacteria Beverage)

Powdered skim milk in an amount of 1700 g, 300 g of glucose and 7700 g of deionized water were mixed and heat-sterilized by keeping at 95° C. for two hours. The mixture was cooled to 37° C., and 300 g of a lactic acid bacterium starter (*Lb. casei*) was inoculated. After stirring and mixing, the mixture was fermented in an incubator kept at 37° C. until the pH reached 4.0. After the pH reached 4.0, the resultant was cooled to 10° C. or lower while stirring, and a fermentation base was thus obtained. In addition, 4 g of the bacterial cells of strain SBT11178 of the Example product 2, 1800 g of caster sugar, 20 g of an acidulant, 10 g of a flavor and 8166 g of deionized water were mixed, and after sterilization at 90° C. for 10 minutes, the mixture was cooled to 10° C. or lower. Thus, a sugar solution was obtained. The fermentation base in an amount of 2000 g and 8000 g of the sugar solution were mixed, and the tissues were smoothed with a homogenizer. The mixture was dispensed to 50 200-ml paper containers and then sealed tightly with aluminum caps, and thus 10 kg of a joint function-improving lactic acid bacteria beverage of the invention was produced. Here, 64 mg of bacterial cells of strain SBT11178 were contained in 200 ml of the joint function-improving lactic acid bacteria beverage of the invention.

Example 13

(Preparation of Joint Function-Improving Soft Drink)

The bacterial cells of strain SBT0320 of the Example product 1 in an amount of 3 g, 0.75 kg of 50% lactic acid, 5.7 kg of erythritol, 1 kg of a flavor and 42.547 kg of deionized water were mixed, and after heating to 40° C., the mixture was stirred and mixed with a TK homogenizing mixer (TK ROBO MICS; manufactured by Tokushu Kika Kogyo Co., Ltd.) at 6,000 rpm for 10 minutes. The solution was sterilized at 90° C. for 10 minutes and then cooled to 10° C. or lower, and thus 50 kg of a joint function-improving soft drink of the invention was produced. Here, 12 mg of bacterial cells of strain SBT0320 were contained in 200 ml of the joint function-improving soft drink of the invention.

Example 14

(Preparation of Joint Function-Improving Cheese)

Gouda cheese in an amount of 9.5 kg, 9.5 kg of Cheddar cheese, 4 g of the bacterial cells of strain SBT2928 of the Example product 3, 200 g of sodium citrate and 796 g of deionized water were mixed and emulsified at 85° C. After the emulsification, the cheese was packed in a carton and cooled for two days and nights at 5° C., and thus 20 kg of joint function-improving cheese of the invention was produced. Here, 20 mg of bacterial cells of strain SBT2928 were contained in 100 g of the joint function-improving cheese of the invention.

Example 15

(Preparation of Joint Function-Improving Margarine)

Hydrogenated soybean oil in an amount of 2 kg, 4 kg of refined soybean oil, 2.5 kg of palm oil and 50 g of glycerol fatty acid ester were mixed, and an oil layer was thus prepared. Next, 20 g of the bacterial cells of strain SBT2785 of the Example product 3, 10 g of lactic acid and 1420 g of deionized water were mixed and added to the oil layer, and a water-in-oil emulsion was thus obtained. The emulsion was cooled, solidified and kneaded with a margarin maker, and thus 10 kg of joint function-improving margarin of the invention was produced. Here, 20 mg of bacterial cells of strain SBT2785 were contained in 10 g of the joint function-improving margarin of the invention.

Example 16

(Preparation of Joint Function-Improving Cream)

Hydrogenated rapeseed oil in an amount of 4.5 kg, 40 g of lecithin, 10 g of monoglycerol fatty acid ester and 10 g of sorbitol fatty acid ester were mixed, and an oil phase was thus prepared. Next, 40 g of the bacterial cells of strain SBT2922 of the Example product 3, 400 g of powdered skim milk, 10 g of sodium caseinate, 20 g of sugar ester, 10 g of a phosphate, 5 g of xanthan gum and 4.955 kg of deionized water were mixed, and thus an aqueous phase was prepared. The aqueous phase was heated to 65° C., and the oil phase heated at 70° C. was added in small amounts with stirring. The mixture was stirred and mixed with a TK homogenizing mixer (TK ROBO MICS; manufactured by Tokushu Kika Kogyo Co., Ltd.) at 6,000 rpm for 10 minutes. The mixture was homogenized with a homogenizer, and thus 10 kg of joint function-improving cream of the invention was produced. Here, 40 mg of bacterial cells of strain SBT2922 were contained in 10 g of the joint function-improving cream of the invention.

Example 17

(Preparation of Joint Function-Improving Puddings)

Honey in an amount of 2000 g, 4 g of the bacterial cells of strain SBT2992 of the Example product 3, 800 g of powdered skim milk, 300 g of mascarpone, 700 g of liquid water, 500 g of granulated sugar, 250 g of fresh cream, 200 g of butter, 400 g of sweetened egg yolk, 40 g of gelatin, 15 g of agar, 120 g of locust bean gum and 4671 g of deionized water were mixed, and thus a pudding mix was obtained. The pudding mix was stirred and mixed with a TK homogenizing mixer (TK ROBO MICS; manufactured by Tokushu Kika Kogyo Co., Ltd.) at 6,000 rpm for 10 minutes, and after dissolving by heating to 60° C., the pudding mix was packed in containers each in an amount of 100 g and cooled. Thus, 100 joint function-improving puddings of the invention were produced. Here, 40 mg of bacterial cells of strain SBT2992 were contained in 100 g of the joint function-improving pudding of the invention.

Example 18

(Preparation of Joint Function-Improving Jellies)

The bacterial cells of strain SBT2687 of the Example product 1 in an amount of 4.4 g, 2000 g of fructose, 1500 g of granulated sugar, 500 g of water, 100 g of agar, 10 g of a flavor and 5885.6 g of deionized water were mixed, and the mixture was stirred and mixed with a TK homogenizing mixer (TK ROBO MICS; manufactured by Tokushu Kika Kogyo Co., Ltd.) at 6,000 rpm for 10 minutes. After dissolving by heating to 50° C., the mixture was packed in containers each in an amount of 100 g and cooled, and thus 100 joint function-improving jellies of the invention were produced. Here, 44 mg of bacterial cells of strain SBT2687 were contained in 100 g of the joint function-improving jelly of the invention.

Example 19

(Preparation of Joint Function-Improving Wafers)

After mixing 9.2 g of the bacterial cells of strain SBT2651 of the Example product 1, 8.5 kg of flour, 1.21 kg of corn starch, 0.22 kg of palm oil and 0.05 kg of baking powder, an adequate amount of deionized water was added, and a batter was thus prepared. Then, by baking with a wafer baker, 10 kg of joint function-improving wafers of the invention were produced. Here, 46 mg of bacterial cells of strain SBT2651 were contained in 50 g of the joint function-improving wafers of the invention.

INDUSTRIAL APPLICABILITY

According to the invention, a joint function-improving composition which can be taken for a long term and is highly safe and which has a significant joint function-improving action through an action of promoting growth of chondrocytes or an action of suppressing the production of an inflammation factor, a cartilage matrix degradation factor, a pain factor or a neuronal outgrowth factor by synoviocytes can be provided. Thus, by taking the invention, various arthropathies such as osteoarthritis including knee osteoarthritis as a typical example and rheumatoid arthritis can be prevented or treated.

ACCESSION NUMBERS

Reference to Deposited Biological Material (1) *Lactobacillus acidophilus* strain SBT2062
(i) Name and Address of Depositary to Which the Biological Material was Deposited
International Patent Organism Depositary, National Institute of Technology and Evaluation
122, 2-5-8 Kazusakamatari, Kisarazu-shi, Chiba, Japan (292-0818)
(ii) Date of Deposit of Biological Material to Depositary of (i)
May 18, 1989
(iii) Accession Number Given to Deposit by Depositary of (i)
FERM BP-11075
(2) *Lactobacillus helveticus* strain SBT2161
(i) Name and Address of Depositary to Which the Biological Material was Deposited
NITE Patent Microorganisms Depositary, National Institute of Technology and Evaluation
122, 2-5-8 Kazusakamatari, Kisarazu-shi, Chiba, Japan (292-0818)
(ii) Date of Deposit of Biological Material to Depositary of (i)
Sep. 18, 2013
(iii) Accession Number Given to Deposit by Depositary of (i)
NITE BP-1707
(3) *Lactobacillus helveticus* strain SBT2171
(i) Name and Address of Depositary to Which the Biological Material was Deposited
International Patent Organism Depositary, National Institute of Technology and Evaluation
122, 2-5-8 Kazusakamatari, Kisarazu-shi, Chiba, Japan (292-0818)
(ii) Date of Deposit of Biological Material to Depositary of (i)
Jun. 22, 1994 (date of original deposit)
Mar. 6, 1996 (date of transfer of original deposit to deposit under Budapest treaty)
(iii) Accession Number Given to Deposit by Depositary of (i)
FERM BP-5445
(4) *Lactobacillus salivarius* strain SBT2687
(i) Name and Address of Depositary to Which the Biological Material was Deposited
NITE Patent Microorganisms Depositary, National Institute of Technology and Evaluation
122, 2-5-8 Kazusakamatari, Kisarazu-shi, Chiba, Japan (292-0818)
(ii) Date of Deposit of Biological Material to Depositary of (i)
Dec. 1, 2020
Dec. 22, 2021 (date of transfer of original deposit to deposit under Budapest treaty)

(iii) Accession Number Given to Deposit by Depositary of
(i)

NITE ABP-03331

(5) *Lactobacillus salivarius* strain SBT2651

(i) Name and Address of Depositary to Which the Biological Material was Deposited NITE Patent Microorganisms Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Dec. 1, 2020

(iii) Accession Number Given to Deposit by Depositary of
(i)

NITE P-03330

(6) *Lactobacillus salivarius* subsp. *salivarius* strain SBT2670

(i) Name and Address of Depositary to Which the Biological Material was Deposited International Patent Organism Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Nov. 6, 1992

(iii) Accession Number Given to Deposit by Depositary of
(i)

FERM P-13247

(7) *Streptococcus oralis* strain SBT0320

(i) Name and Address of Depositary to Which the Biological Material was Deposited NITE Patent Microorganisms Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Dec. 1, 2020

(iii) Accession Number Given to Deposit by Depositary of
(i)

NITE P-03332

(8) *Lactococcus lactis* subsp. *lactis* strain SBT0625

(i) Name and Address of Depositary to Which the Biological Material was Deposited NITE Patent Microorganisms Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Nov. 25, 2019

(iii) Accession Number Given to Deposit by Depositary of
(i)

NITE P-03078

(9) *Lactococcus lactis* subsp. *cremoris* strain SBT11373

(i) Name and Address of Depositary to Which the Biological Material was Deposited NITE Patent Microorganisms Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Jul. 14, 2020

26

(iii) Accession Number Given to Deposit by Depositary of
(i)

NITE P-03246

(10) *Lactococcus laudensis* strain SBT11178

(i) Name and Address of Depositary to Which the Biological Material was Deposited NITE Patent Microorganisms Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Dec. 1, 2020

(iii) Accession Number Given to Deposit by Depositary of
(i)

NITE P-03333

(11) *Bifidobacterium longum* strain SBT2928

(i) Name and Address of Depositary to Which the Biological Material was Deposited International Patent Organism Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Apr. 13, 1989

(iii) Accession Number Given to Deposit by Depositary of
(i)

FERM P-10657

(12) *Bifidobacterium longum* subsp. *infantis* SBT Strain 2785

(i) Name and Address of Depositary to Which the Biological Material was Deposited NITE Patent Microorganisms Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Dec. 1, 2020

(iii) Accession Number Given to Deposit by Depositary of
(i)

NITE P-03328

(13) *Bifidobacterium pseudolongum* strain SBT2922

(i) Name and Address of Depositary to Which the Biological Material was Deposited NITE Patent Microorganisms Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Jun. 26, 2019

(iii) Accession Number Given to Deposit by Depositary of
(i)

NITE P-02984

(14) *Bifidobacterium thermophilum* strain SBT2992

(i) Name and Address of Depositary to Which the Biological Material was Deposited NITE Patent Microorganisms Depositary, National Institute of Technology and Evaluation

122, 2-5-8 Kazusakamatari, Kisarazu-shi, Chiba, Japan (292-0818)

(ii) Date of Deposit of Biological Material to Depositary of (i)

Jan. 19, 2021

(iii) Accession Number Given to Deposit by Depositary of (i)

NITE P-03364

The invention claimed is:

1. A method for improving joint function comprising administering orally to a subject in need thereof a formulation consisting of:
   2 to 100 mg of bacterial cells belonging to *Lactobacillus salivarius*; and
   a diluent or an excipient,
wherein the bacterium belonging to *Lactobacillus salivarius* is *Lactobacillus salivarius* strain SBT2687, accession number NITE BP-03331, NITE Patent Microorganisms Depositary, National Institute of Technology and Evaluation.

* * * * *